United States Patent
Jansson et al.

(10) Patent No.: US 9,445,908 B2
(45) Date of Patent: Sep. 20, 2016

(54) ELEVATED IMPLANT FOR THE RECONSTRUCTION OF MENISCUS DEFECTS OR PARTIAL MENISCUS DEFECTS

(75) Inventors: Volkmar Jansson, Gilching (DE); Peter Mueller, Landsberg am Lech (DE)

(73) Assignee: Aesculap AG (DE)

( * ) Notice: Subject to any disclaimer, the term of this patent is extended or adjusted under 35 U.S.C. 154(b) by 471 days.

(21) Appl. No.: 12/828,407

(22) Filed: Jul. 1, 2010

(65) Prior Publication Data

US 2011/0004305 A1    Jan. 6, 2011

(30) Foreign Application Priority Data

Jul. 6, 2009  (DE) .................. 10 2009 032 218

(51) Int. Cl.
*A61F 2/38*    (2006.01)
*A61F 2/30*    (2006.01)

(52) U.S. Cl.
CPC ............... *A61F 2/38* (2013.01); *A61F 2/3872* (2013.01); *A61F 2/30965* (2013.01); *A61F 2002/30014* (2013.01); *A61F 2002/30062* (2013.01); *A61F 2002/3092* (2013.01); *A61F 2002/30156* (2013.01); *A61F 2002/30281* (2013.01); *A61F 2002/30308* (2013.01); *A61F 2210/0004* (2013.01); *A61F 2230/0023* (2013.01); *A61F 2230/0063* (2013.01); *A61F 2230/0086* (2013.01); *A61F 2250/0018* (2013.01)

(58) Field of Classification Search
CPC .................................................... A61F 2/3872
USPC ........................................................ 623/14.12
See application file for complete search history.

(56) References Cited

U.S. PATENT DOCUMENTS

| | | | |
|---|---|---|---|
| 4,919,667 A | | 4/1990 | Richmond |
| 5,711,960 A | * | 1/1998 | Shikinami ............... 424/426 |
| 5,855,610 A | * | 1/1999 | Vacanti ............... A61L 27/18 623/2.13 |
| 2001/0016772 A1 | | 8/2001 | Lee et al. |
| 2002/0022884 A1 | * | 2/2002 | Mansmann ........... A61F 2/3872 623/14.12 |
| 2002/0183845 A1 | * | 12/2002 | Mansmann ............... 623/13.11 |
| 2005/0209703 A1 | * | 9/2005 | Fell ............................ 623/20.33 |
| 2006/0160734 A1 | | 7/2006 | Kusanagi et al. |
| 2006/0173542 A1 | * | 8/2006 | Shikinami ................. 623/14.12 |
| 2007/0148242 A1 | * | 6/2007 | Vilei et al. .................... 424/484 |
| 2008/0086210 A1 | | 4/2008 | Fox |
| 2008/0097606 A1 | | 4/2008 | Cragg et al. |
| 2009/0259311 A1 | | 10/2009 | Shterling et al. |

FOREIGN PATENT DOCUMENTS

| | | |
|---|---|---|
| DE | 38 40 470 A1 | 6/1990 |
| DE | 689 06 516 T2 | 9/1993 |
| DE | 20 2008 013581 | 3/2009 |
| EP | 0 053 460 A1 | 6/1982 |

(Continued)

*Primary Examiner* — David Isabella
*Assistant Examiner* — Suba Ganesan
(74) *Attorney, Agent, or Firm* — DLA Piper LLP (US)

(57) ABSTRACT

An implant for reconstructing meniscus defects or partial meniscus defects includes an elevated molding with a femoral condylar contact area, a tibial condylar contact area and an articular capsule contact area, in the manner of an artificial meniscus or artificial partial meniscus with a contour of an outer area that is substantially the same as a natural meniscus or partial meniscus, wherein at least one additional elevation is formed on the outer area of the elevated molding.

21 Claims, 3 Drawing Sheets

(56) References Cited

FOREIGN PATENT DOCUMENTS

EP      0 461 201  B1    12/1991

WO      03/007788         1/2003
WO      2007/020449  A2   2/2007
WO      2009/052208  A2   4/2009

* cited by examiner

ELEVATED IMPLANT FOR THE RECONSTRUCTION OF MENISCUS DEFECTS OR PARTIAL MENISCUS DEFECTS

RELATED APPLICATION

This application claims priority of German Patent Application No. 10 2009 032 218.3, filed Jul. 6, 2009, herein incorporated by reference.

TECHNICAL FIELD

This disclosure relates to an implant for reconstructing meniscus defects or partial meniscus defects, a corresponding surgical set and a method for reconstructing meniscus defects or partial meniscus defects.

BACKGROUND

The treatment of meniscus defects represents one of the great challenges in orthopedics and accident surgery. It had long been held that destruction of the meniscal structures is irreversible and that total restoration "restitutio ad integrum" is no longer possible.

There have in the meantime been a series of good attempts at the treatment of meniscus defects. As before, however, only a few suitable implants are available so far. In some cases, meniscus transplants from donor bodies are also used. It is disadvantageous, however, that the material concerned is dead and therefore can only be revitalized under certain conditions.

A key problem with meniscus reconstructions is the stable anchorage of the implant or transplant. Since perfusion of the meniscus takes place from what is known as the base, i.e., from the side of the meniscus facing the articular capsule, every implant or transplant must be anchored as firmly as possible by its base to this articular capsule or cartilage rim. If stable anchorage on the articular capsule does not occur, it may be the case, for example, that a transplant is not revitalized. Stable anchorage in the healing phase, in the sense of close contact between the meniscus transplant or implant and the articular capsule, must also additionally withstand movements of the joint.

Usually, implants or transplants used for meniscus reconstruction are fixed to the articular capsule by a similar technique to that also used for treating meniscus ruptures. In this technique, the implants or transplants are sewn in with threads or attached to the articular capsule by suitable anchoring elements. In this case, the anchoring elements are fired into the articular capsule through the meniscus to be attached, the implant to be attached or the transplant to be attached. A particular problem here is also fixing the end points of a meniscus implant or transplant. One of the usual fixing techniques is to reinforce the end points with the threads and anchor the threads in the tibial bone.

In spite of all these efforts, the results achieved in the treatment of cartilage and meniscus defects are still not satisfactory. In particular, the treatment methods described above are laborious and time-consuming. It is even often necessary for the joint to be partially opened in an arthrotomy procedure. Furthermore, it is often technically very difficult to use arthroscopic means for introducing anchoring elements into the desired position. In US 2008/0086210 A1, anchorage elements for anchoring the artificial meniscus described there engage in a groove in the tibial bone, which is difficult to carry out intraoperatively. Furthermore, the anchorage does not take place on the articular capsule but on the articular bone.

It could therefore be helpful to provide an implant for meniscus reconstruction that allows the most stable possible anchorage or fixing on the articular capsule (cartilage rim) of a patient. In addition, the implant should be as easy as possible to implant, in particular by arthroscopic methods.

SUMMARY

We provide an implant for reconstructing meniscus defects or partial meniscus defects including an elevated molding with a femoral condylar contact area, a tibial condylar contact area and an articular capsule contact area, in the manner of an artificial meniscus or artificial partial meniscus with a contour of an outer area that is substantially the same as a natural meniscus or partial meniscus, wherein at least one additional elevation is formed on the outer area of the elevated molding.

We also provide a surgical set for reconstructing meniscus defects or partial meniscus defects, including at least one implant.

BRIEF DESCRIPTION OF THE DRAWINGS

Further features and advantages emerge from the following description on the basis of the description of the figures and the figures themselves. The features may be realized in each case on their own or in combination with one another.

In the schematic figures.

DETAILED DESCRIPTION

It will be appreciated that the following description is intended to refer to specific examples of structure selected for illustration in the drawings and is not intended to define or limit the disclosure, other than in the appended claims.

The implant is for reconstructing meniscus defects or partial meniscus defects, comprising an elevated molding with a femoral condylar contact area, a tibial condylar contact area and an articular capsule contact area, in particular, in the manner of an artificial meniscus or artificial partial meniscus with a contour of the outer area that is substantially the same as a natural meniscus or partial meniscus, at least one, in particular one, additional elevation being formed on the outer area or surface of the elevated molding. There may also be two, three, four or more additional elevations provided, if need be.

An elevated molding is to be understood as meaning a molding which has an elevation or superelevation. An elevation is to be understood as meaning a transverse slope of the molding. If, for example, the molding is of a curved form, as explained in more detail below, the transverse slope or elevation is preferably formed in the curve region of the elevated molding toward the interior of the curve.

We provide an implant for the reconstruction of meniscus defects or partial meniscus defects on the basis of an elevated molding which can be formed as an artificial meniscus or artificial partial meniscus and is additionally elevated on its outer area or surface. If the implant is introduced in place of a previously removed, defective meniscus or partial meniscus between the articular surface areas of a patient's knee, which can be carried out particularly advantageously arthroscopically, the implant is pressed outward onto the articular capsule (cartilage rim) and held there with greater force than in the case of artificial menisci or artificial partial menisci known from the prior art, as a result of the additional elevation provided by the femoral and tibial articular condyles. Additional fixing steps, in particular, to the articular capsule or cartilage rim of a human or animal knee joint, are generally no longer required.

Preferably, the superelevated molding and the at least one additional elevation are formed in one piece. For example, the elevated molding and the at least one additional elevation may be monolithically formed. It is preferred if the at least one additional elevation is formed onto the outer area of the elevated molding. The elevated molding and the at least one additional elevation may be connected to each other by a force fit, a form fit and/or a material bond, with preference a material bond. Suitable material-bonded connections may be based, for example, on adhesive, welding, soldering, pressing, coating and/or lyophilizing techniques.

Further preferably, the implant has a compound structure comprising the elevated molding and the at least one additional elevation, in particular, in the manner of a composite. In particular, the elevated molding and the at least one additional elevation may touch along a common boundary surface. Preferably, the elevated molding and the at least one additional elevation are connected to each other along a common boundary surface. With respect to suitable possibilities for connection, reference is made to the examples described in the previous paragraph.

The at least one additional elevation may take the form of a coating on the outer area of the elevated molding.

The at least one additional elevation is preferably formed on at least part, in particular only on part, of the outer area of the elevated molding. The at least one additional elevation is in this case generally formed over the full surface area on the at least one part of the outer area of the elevated molding. In principle, the at least one additional elevation may be formed on the femoral condylar contact area, tibial condylar contact area and/or the articular capsule contact area of the elevated molding. With preference, the at least one additional elevation is formed on the femoral condylar contact area or tibial condylar contact area of the elevated molding. If the at least one additional elevation is formed on the articular capsule contact area of the elevated molding, it is preferred if it is also additionally formed on the femoral and/or tibial condylar contact area of the elevated molding, whereby the elevated molding is particularly advantageously pressed outward onto the articular capsule or cartridge rim.

The implant may have two additional elevations. For example, an additional elevation may be respectively formed on the femoral condylar contact area and tibial condylar contact area of the elevated molding. Alternatively, an additional elevation may also be respectively formed on the outer area of end regions of the elevated molding. Additional elevations formed on end regions of the elevated molding are ideally formed in such a way that they can correspond to the contour of the outer area of the articular portions of the femur and the tibia that are adjacent the end regions of the elevated molding, so that firm anchorage or clamping of the implant is possible in particular in the region of these end regions.

The implant, in particular the elevated molding and/or the at least one additional elevation, may be of such a form that it can be resorbed, can be partially resorbed and/or cannot be resorbed. Preferably, the implant, in particular the elevated molding and the at least one additional elevation, is of such a form that it can be resorbed.

In principle, the at least one additional elevation may be formed from the same material as the elevated molding.

Preferably, however, the at least one additional elevation is formed from a different material than the elevated molding. With preference, the at least one additional elevation is formed from a resorbable material, with greater preference from a different resorbable material, with particular preference from a more quickly resorbable material than the elevated molding. If the at least one additional elevation is formed such that it can be resorbed or resorbed more quickly than the elevated molding, this has the advantage that it is merely during the initial healing phase that there is increased pressing of the implant against the articular capsule or cartridge rim of a patient. In the further course of the healing phase, the pressure on the implant decreases substantially continuously, as a result of the resorbability or quicker resorbability of the at least one additional elevation. Ideally, regenerated meniscus that is built up by body cells of the patient and/or possibly cells located in the elevated molding takes the place of the at least one additional elevation after the resorption.

The at least one additional elevation may have a layered structure. Preferably, individual layers of the at least one additional elevation are formed from materials with different resorption rates or resorption times. Preferably, layers of the at least one additional elevation that are facing an articular area, in particular a femoral and/or tibial articular area, have a faster resorption rate than layers lying thereunder, in particular of the at least one additional elevation. It is particularly preferred if layers of the at least one additional elevation form a resorption gradient. Preferably, the resorption rate of the layers increases substantially continuously from a side of the at least one additional elevation that is facing the elevated molding to an opposite side of the at least one additional elevation that is facing a femoral and/or tibial articular area. In other words, it is particularly advantageous if the at least one additional elevation has a layered structure with respect to the resorption time or resorption rate. This makes it possible in particular for layers of the at least one additional elevation that are facing the articular areas to resorb more quickly, whereby the thickness of the at least one additional elevation decreases during the healing phase, so that the implant or the elevated molding is finally subjected to loading under physiological conditions.

The at least one additional elevation may have a substantially smooth outer area. In other words, it is advantageous if the material of the at least one additional elevation has good sliding properties. Furthermore, it may be advantageous if the at least one additional elevation has a low-friction outer area. In other words, it is also advantageous if the material of the at least one additional elevation has good tribological properties. Preferably, the outer area of the at least one additional elevation is formed such that it is smooth and has little friction. This improves the articulation of the at least one additional elevation with the articular surfaces of the knee joint. It may also be provided that the at least one additional elevation is covered toward the joint by a low-friction and, in particular, smooth membrane.

The at least one additional elevation may be formed from a flexible and, in particular, soft material. With preference, the at least one additional elevation is formed from a more flexible and, in particular, softer material than the elevated molding. Furthermore, the at least one additional elevation may be formed from a stretchable, in particular elastic, material. Preferably, the at least one additional elevation is formed from a more flexible, in particular softer, material than the elevated molding.

Preferably, the implant, in particular the elevated molding and/or the at least one additional elevation, is of a porous form. The implant, in particular the elevated molding and/or the at least one additional elevation, preferably has an interconnecting porosity. The implant, in particular the elevated molding and/or the at least one additional elevation, may have pores with a pore size of between 50 and 500 µm, with preference 100 and 350 µm, with particular preference 150 and 250 µm. Preferably, the implant, in particular the elevated molding and/or the at least one additional elevation, is of an open-pore form. In principle, the implant, in particular the elevated molding and/or the at least one additional elevation, may be of an open-pore form in the region of the femoral condylar contact area, tibial condylar contact area and/or the articular capsule contact area.

With preference, the implant, in particular the elevated molding and/or the at least one additional elevation, is of an open-pore form in the region of the articular capsule contact area, in particular only in the region of the articular capsule contact area. This is particularly advantageous since the natural meniscus has cells substantially only in its region that is facing the articular capsule (known as the base).

By contrast, the other regions of a natural meniscus, in particular the regions facing the femoral and tibial articular surfaces, have decidedly few cells. As a result, body cells, in particular stem cells, chondrocytes, chondroblasts and/or fibroblasts, of the patient originating from the articular capsule can colonize the implant, in particular the elevated molding and/or the at least one additional elevation, and contribute to a permanent anchorage of the implant, in particular the elevated molding and/or the at least one additional elevation, on the articular capsule of the patient by the buildup of the body's own connective tissue, in particular cartilage tissue.

With preference, the implant, in particular the elevated molding and/or the at least one additional elevation, has open pores on the articular capsule contact area, pores which are formed to a depth that corresponds to one third or two thirds of the width of the implant, in particular the elevated molding and/or the at least one additional elevation. If, on the other hand, only body cells from the synovial fluid are intended to grow into the implant, in particular the elevated molding and/or the at least one additional elevation, the implant, in particular the elevated molding and/or the at least one additional elevation, is of an open-pore form preferably only in the region of the femoral condylar contact area and/or tibial condylar contact area.

Alternatively, the implant, in particular the elevated molding and/or the at least one additional elevation, is of an open-pored form in the region of the femoral condylar contact area, tibial condylar contact area and the articular capsule contact area. In this way, both ingrowth of body cells from the synovial fluid, known as synovial cells, and ingrowth of other body cells, in particular stem cells, chondrocytes, chondroblasts and/or fibroblasts originating from the articular capsule of the patient into the implant, in particular the elevated molding and/or the at least one additional elevation, are possible.

The implant, in particular the elevated molding and/or the at least one additional elevation, may have closed pores. As a result, the flexibility, in particular stretchability, preferably elasticity, of the implant, in particular the elevated molding and/or the at least one additional elevation, can be increased with particular advantage in the sense of easier compressibility, whereby better adaptation to individual contours of the patient's joint is possible. It may be provided in this respect that merely the at least one additional elevation, in particular only layers thereof that are facing articular surfaces, have closed pores.

Further advantageously, the implant, in particular the elevated molding and/or the at least one additional elevation, has closed pores and open pores. For example, the implant, in particular the elevated molding and/or the at least one additional elevation, may be of an open-pore form in the region of the articular capsule contact area and of a closed-pore form in the region of the femoral condylar contact area and/or tibial condylar contact area. In this way, for example, in ingrowth of body cells originating from the articular capsule of a patient into the implant, in particular the elevated molding and/or the at least one additional elevation, is facilitated. By contrast, the closed pores in the region of the femoral condylar contact area and/or tibial condylar contact area of the implant, in particular the elevated molding and/or the at least one additional elevation, provide greater flexibility, in particular stretchability, preferably elasticity, with particular advantage, whereby in turn better adaptation to specific contours of the patient's joint can be achieved.

The implant, in particular the elevated molding and/or the at least one additional elevation, may have pores filled with a material. The pores may in this case be at least partially or completely filled with the material. The material itself is, with preference, a resorbable and/or viscous, in particular highly viscous, material. As a result, the implant, in particular the elevated molding and/or the at least one additional elevation, can be provided with stability that is adequate from physiological aspects. If the filling material is resorbable and/or viscous, in particular highly viscous, space for ingrowing body cells, in particular stem cells, chondrocytes, chondroblasts, synovial cells, fibroblasts and combinations thereof, is available as resorption progresses or as the emergence of the material from the pores progresses. With preference, the implant, in particular the elevated molding and/or the at least one additional elevation, has in the region of the articular capsule contact area, preferably merely in the region of the articular capsule contact area, pores filled with a material. If, as described above, the material is resorbable or viscous, in particular highly viscous, cellular colonization originating from the articular capsule of a patient into the implant, in particular the elevated molding and/or the at least one additional elevation, can be "enforced" with particular advantage.

Areas of the implant, in particular the elevated molding and/or the at least one additional molding, that are facing the articular cartridge may be closed or covered by a membrane, which optionally has good tribological properties.

The membrane preferably allows the diffusion of articular fluid for the nutrition of cells.

The implant, in particular the elevated molding and/or the at least one additional elevation, may be of a disk-shaped form, in particular in the form of a cylindrical disk, or a substantially wedge-shaped form. In particular, the implant, in particular the elevated molding and/or the at least one additional elevation, has a wide central region, which is flanked by two narrow end regions in relation thereto. With preference, the implant, in particular the elevated molding and/or the at least one additional elevation, is of a semicircular, C-shaped, sickle or crescent-shaped form. The implant, in particular the elevated molding and/or the at least one additional elevation, may also take the form of a wedge widened in a circular manner, in particular a wedge widened in a sickle- or crescent-shaped manner. If the implant, in particular the elevated molding and/or the at least one additional elevation, takes the form of a wedge, this wedge preferably has a central region and a peripheral region, the peripheral region preferably extending over an angle of more than 0° and ≤360° around the central region and the peripheral region may have a greater thickness than the central region of the wedge.

The implant, in particular the elevated molding and/or the at least one additional elevation, may have anchorage elements for anchoring the implant, in particular the elevated molding and/or the at least one additional elevation, to the knee joint of a patient. The anchorage elements may, in principle, be intended for anchoring the implant, in particular the elevated molding and/or the at least one additional elevation, to the femoral bone, tibial bone and/or the articular capsule. In principle, the anchorage elements may therefore be formed in the region of the femoral condylar contact area, the tibial condylar contact area and/or the articular capsule contact area of the implant, in particular the elevated molding and/or the at least one additional elevation. Preferably, the anchorage elements are formed in the region of the articular capsule contact area. Suitable anchorage elements are selected from the group comprising anchor hooks, in particular barbs, anchor flukes, anchor pins, anchor screws and filamentary structures, in particular threads. Combinations of the anchorage elements listed above are likewise conceivable.

The anchorage elements are generally formed in one piece with the implant, in particular the elevated molding and/or the at least one additional elevation. For example, the anchorage elements may be fastened to the implant, in particular to the elevated molding and/or the at least one additional elevation, before the implantation. The anchorage elements themselves preferably consist of a resorbable material. Furthermore, it is of advantage if the anchorage elements are formed from a material which can, for example, be pressed into the articular capsule or cartilage rim of a patient, whereby better anchorage of the implant according to the invention, in particular the elevated molding and/or the at least one additional elevation, can be achieved on account of the form fit and/or material bond that can be achieved thereby.

A further advantage is that targeted, controllable injury and inflammation stimuli can be caused by means of anchorage elements, whereby ingrowth of the implant, in particular the elevated molding and/or the at least one additional elevation, is promoted in the region of the knee joint of a patient. If the anchorage elements are threads, these threads may be threads that are firmly incorporated in the implant, in particular the elevated molding, and emerge from it. With the aid of threads as anchorage elements, the implant can, in particular, be sewn onto the articular capsule or cartilage rim of a patient, optionally with the aid of suitable instruments. The use of threads as anchorage elements also has the advantage that, after a certain time, they can be integrated in the connective tissue of a patient and in this way similarly promote the ingrowth of the implant, in particular the elevated molding and/or the at least one additional elevation, on the articular capsule of a patient.

The implant, in particular the elevated molding and/or the at least one additional elevation, may have anchorage elements, in particular as described in the previous paragraph, only in the region of the femoral condylar contact area and/or tibial condylar contact area. In this connection, threads are mentioned as particularly preferred anchorage elements. These can be drawn through a human or animal bone and fastened to it by means of corresponding instruments. Alternatively, the threads may be connected at their free end by means of one or more other anchorage elements. The threads connected to one or more other anchorage elements may be fixed in the bone with the aid of a suitable instrument and the threads may optionally be tightened to achieve a desired pretension. However, it is similarly possible for the anchorage elements to have structures in the form of barbs, whereby they can, for example, be anchored in the tissue of the articular capsule of a patient and in this way the implant, in particular the elevated molding and/or the at least one additional elevation, can be stabilized in the region of the femoral condylar contact area and/or tibial condylar contact area.

As already mentioned, the implant is also suitable for the reconstruction of partial meniscus defects. In other words, the implant may be formed as a partial artificial meniscus. In particular, the anchorage elements described in the previous examples may be used here. In particular, it may be provided that an implant formed as a partial artificial meniscus has anchorage elements at the ends thereof at which it touches the natural meniscus that is left behind in the joint. The anchorage elements may be pressed into the natural residual meniscus and become connected in a firm way to the natural residual meniscus, for example, by means of a form fit. The anchorage elements may, furthermore, either be firmly connected to the implant or else be connected to the implant and/or be anchored in the natural residual meniscus immediately before the operation. As an alternative thereto or in combination therewith, it may be advisable to adhesively bond the implant that is formed as a partial artificial meniscus to a natural residual meniscus, for example, by a fibrin adhesive and/or tissue adhesive based on cyanoacrylate monomers. To improve the adhesive attachment of the adhesive to the partial artificial meniscus, sides of the implant formed as a partial artificial meniscus that are lying against the natural meniscus may be roughened or provided with a coating which becomes connected particularly well to the adhesive that is used. It is also possible to allow threads to which the adhesive that is used bonds particularly well to protrude from the areas of the implant that are lying against the natural residual meniscus. With preference, threads which, on account of their material properties or an account of a surface coating, can be connected particularly well to an adhesive are used here.

Meniscus defects are often also located at the end points of a natural meniscus. In these cases, it is of advantage if an implant formed as a partial artificial meniscus has anchorage elements on the side lying against the natural residual meniscus.

The implant may have anchorage elements for an anchorage between the elevated molding and the at least one additional elevation.

The implant, in particular the elevated molding, may have a spacer, which is intended for maintaining a distance between the femoral and tibial articular surfaces. It is particularly preferred for the at least one additional elevation also to be formed as a spacer, in particular for maintaining a distance between the femoral and tibial articular surfaces. The spacer may extend up to the notch region of the knee joint or even into the notch region (roof between the femur condyles or the fossa intercondylaris) of the knee joint. Since the spacer generally lies between the articular surfaces of the femur and the tibia and is preferably adapted to the form of the femur condyles and the tibia condyles, and can consequently be placed stably between these articular surfaces, the spacer brings about additional stabilization of the implant in the joint. It is particularly preferred if the spacer has a shorter resorption time than the elevated molding (artificial meniscus or artificial partial meniscus). The spacer and the elevated molding may be formed in one piece or be physically separate from each other. If the spacer and the elevated molding are not firmly connected to each other, the spacer may, for example, be supported against the articular surfaces of the femoral and tibial tibia condyles as well as against the elevated molding, whereby the implant, in particular the elevated molding and/or the at least one additional elevation, is pressed outward against the articular capsule or cartilage rim. In this way, the anchorage in the region of the articular capsule of the knee joint of a patient can be further improved.

The implant, in particular the elevated molding and/or the at least one additional elevation, can, in principle, include any and all biocompatible materials or be formed from any and all biocompatible materials. The materials may be such that they can be resorbed, can be partially resorbed or cannot be resorbed. With preference, the implant, in particular the elevated molding and/or the at least one additional elevation, includes a resorbable material or is formed from such a resorbable material. With preference, the materials that come into consideration are naturally occurring polymers, known as biopolymers, and/or synthetic polymers.

Polymers which are comparable with respect to their elastic properties to a natural articular cartilage and/or meniscus tissue are generally preferred. Suitable polymers are selected with preference from the group comprising proteins, polysaccharides, polyhydroxyalkanoates and combinations thereof. Suitable polysaccharides are selected in particular from the group comprising glycosaminoglycans, cellulose derivatives and combinations thereof. The cellulose derivatives may be, in particular, alkyl celluloses, hydroxyalkyl celluloses, carboxyalkyl celluloses or combinations thereof. Preferred polyhydroxyalkanoates are derived from $\alpha$, $\beta$, and/or $\gamma$-hydroxy acids. Suitable biopolymers and/or synthetic polymers may, for example, be selected from the group comprising albumin, gelatin, collagen, elastin, reticulin, chondroitin-4-sulfate, chondroitin-6-sulfate, keratane sulfate, dermatane sulfate, heparin sulfate, hyaluronic acid, chitosan, alginin acid, methyl cellulose hydroxymethyl cellulose, hydroxyethyl cellulose, hydroxypropyl cellulose, hydroxybutyl cellulose, carboxymethyl cellulose, polyactide, polyglycolide, poly-$\epsilon$-caprolactam, polytrimethylene carbonate, poly-para-dioxanone, poly-3-hydroxybutyrate, poly-4-hydroxybutyrate, polyvinyl alcohol, polyurethanes, derivatives thereof, analogs thereof, copolymers thereof and combinations thereof. Suitable polyurethanes may, in particular, be selected from the group comprising aromatic polycarbonate urethanes, aliphatic polycarbonate urethanes, silicone-polycarbonate urethanes, silicone-polyether urethanes, derivatives thereof, analogs thereof and combinations thereof.

The implant, in particular the elevated molding and/or the at least one additional elevation, may be formed from a transplantation material, in particular alloplastic and/or autologous transplantation material. The transplantation material is preferably a connective and/or supportive tissue, in particular cartilage tissue.

The implant, in particular the elevated molding and/or the at least one additional elevation, may have a proportion of a fibrous material. The fibrous material allows the mechanical stability of the implant, in particular the elevated molding and/or the at least one additional elevation, to be improved with particular advantage. Suitable fibrous materials may, for example, be selected from the group comprising polyglycolide, polyactide, polytrimethylene carbonate, poly-$\epsilon$-caprolactam, poly-para-dioxanone, cellulose or cellulose derivatives, hyaluronic acid and combinations thereof. Preferably, the implant, in particular the elevated molding and/or the at least one additional elevation, has an inhomogeneous fiber orientation. For example, in the case of an implant of a semicircular, cresent- or crescent-shaped form, fibers of the fibrous material may be oriented in the radial direction. If the implant has a spacer, fibers of the fibrous material may be arranged in the longitudinal and/or transverse direction of the spacer. With preference, the implant, in particular the elevated molding and/or the at least one additional elevation, has a proportion of the fibrous material of between 2 and 80% by weight, in particular 10 and 30% by weight, preferably 15 and 25% by weight, with respect to the overall weight of the implant.

The implant, in particular the elevated molding and/or the at least one additional elevation, may be inoculated with cells, in particular body cells, preferably autologous body cells. The cells are preferably selected from the group comprising chondrocytes, chondroblasts, synovial cells, fibroblasts, precursor cells thereof, stem cells thereof and combinations thereof. The presence of body cells in the implant, in particular the elevated molding and/or the at least one additional elevation, allows the buildup of a regenerated meniscus to be speeded up. The cells themselves may, for example, originate from the bone marrow of a patient or be taken from the body of a patient during an operation.

Furthermore, the implant, in particular the elevated molding and/or the at least one additional elevation, may contain active substances, in particular biological active substances. The active substances may be selected from the group comprising growth factors, recruitment factors, differentiation factors, adhesion factors and combinations thereof. By means of such active substances, faster cell colonization in the implant and, in particular, faster differentiation of cells growing into the implant, can be achieved in connective tissue, in particular cartilage tissue. The active substances may be, for example, chondro-inductive, fibroblast-inductive, fibroblast-conductive and/or angiogenesis-stimulating.

With preference, the implant, in particular the elevated molding and/or the at least one additional elevation, has chondro-inductive, fibroblast-inductive, fibroblast-conductive and/or angiogenesis-stimulating active substances in the region of the articular capsule contact area, whereas other regions, in particular the femoral conduct contact area and/or the tibial condylar contact area, of the implant, in particular the elevated molding and/or the at least one additional elevation, have with preference chondro-inductive active substances. Furthermore, suitable active substances may also be selected from the group comprising antimicrobial active substances, disinfecting active substances, anti-inflammatory active substances, antalgesic active substances and combinations thereof.

It may also be provided that the active substances are distributed inhomogeneously in the implant, in particular the elevated molding and/or the at least one additional elevation. For example, the active substances may be present in higher concentrations in the region of the articular capsule contact area of the implant than in other regions of the implant.

It is further preferred if, for example, the concentration of growth factors, recruitment factors, differentiation factors, adhesion factors and/or combinations thereof is higher in the region of the articular capsule contact area of the implant than in other regions. This allows the growth of body cells originating from the articular capsule to be speeded up. In particular, anchorage elements of the implant that are optionally provided, in particular the elevated molding and/or the at least one additional elevation, may contain active substances such as those described above or be formed from materials with a corresponding effect.

We also provide a surgical set for the reconstruction of meniscus defects or partial meniscus defects, the surgical set comprising at least one implant. Furthermore, the set may comprise a component selected from the group comprising spacers for keeping a distance between a femoral condyle and a tibial condyle and/or a tissue adhesive. With respect to further features and details, reference is made to the previous description in full.

We further provide a method for the reconstruction of meniscus defects or partial meniscus defects, an implant being implanted after removal of a natural meniscus or partial meniscus between a tibial condyle and a femoral condyle, articulating with the tibial condyle, of a natural knee joint. It may in this case be provided that the tibial condyle and/or the femoral condyle are subjected to microfracturing before the implantation of the implant. Furthermore, it may be provided that the implant is inoculated before implantation with cells, with preference body cells, in particular autologous body cells, preferably selected from the group comprising chondrocytes, chondroblasts, synoviocytes, fibroblasts, precursor cells thereof, stem cells thereof and combinations thereof.

Figure 1:
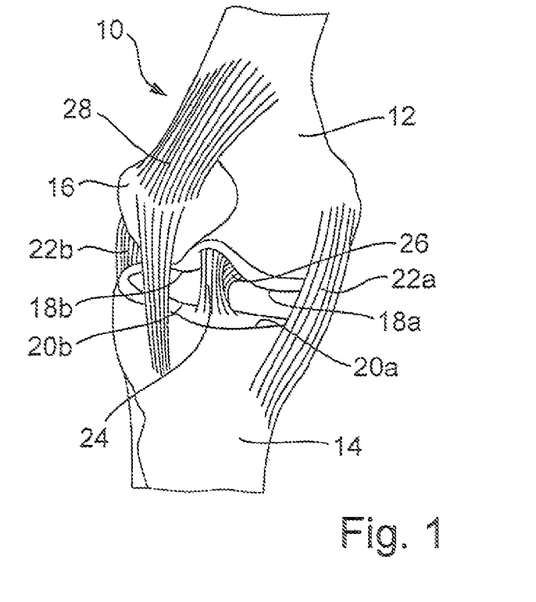
FIG. 1 shows a natural knee joint.

Turning now to the drawings, FIG. 1 shows a natural knee joint 10. The articulating elements involved in the bony structure of the knee joint are the thighbone 12 (femur), the shinbone 14 (tibia) and the kneecap 16 (patella). The thighbone ends toward the knee (distally) with two relatively wide, slightly outwardly curved (convex), condyles 18a; b (Condylus lateralis femoris 18a and Condylus medialis femoris 18b). The upper end of the shinbone 14 likewise ends in two, though slightly inwardly curved (concave), condyles 20a; b (Condylus lateralis tibiae 20a and Condylus medialis tibiae 20b). Between the articular surfaces described above lie the medial meniscus and the lateral meniscus as a pair of crescent-shaped fibrous cartilage disks to compensate for the incongruence of the articular bones (the minisci are not shown in FIG. 1). Of the ligaments likewise involved in the structure of the knee joint, in FIG. 1 the lateral ligaments 22a; b (Ligamentum collaterale fibulare 22a and Ligamentum collaterale tibiale 22b), the front cruciate ligament 24 (Ligamentum cruciatum anterius), the rear cruciate ligament 26 (Ligamentum cruciatum posterior) and the kneecap ligament 28 (Ligamentum patellae) are shown.

Figure 2:
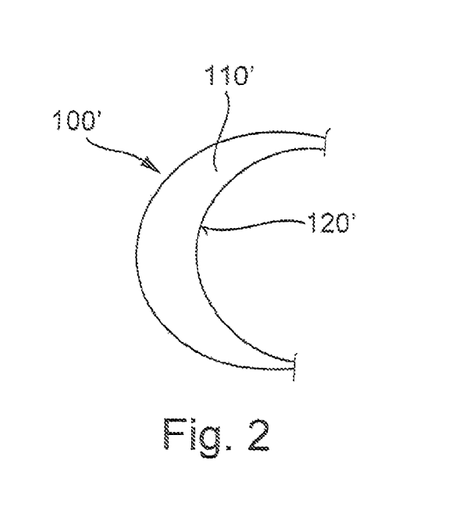
FIG. 2 shows a plan view of an artificial meniscus known from the prior art.

FIG. 2 shows a plan view of an artificial meniscus 100' known from the prior art. The artificial meniscus has a femoral condylar contact area 110', a tibial condylar contact area 120' and an articular capsule or cartilage rim contact area 130' (base). The artificial meniscus 100' is of a sickle- or crescent-shaped form. The artificial meniscus 100' represented in FIG. 2 is suitable for a complete meniscus reconstruction. On account of the open sickle shape given by way of example in FIG. 2, the artificial meniscus 100' is particularly suitable for a reconstruction of the medial meniscus.

Figure 3:
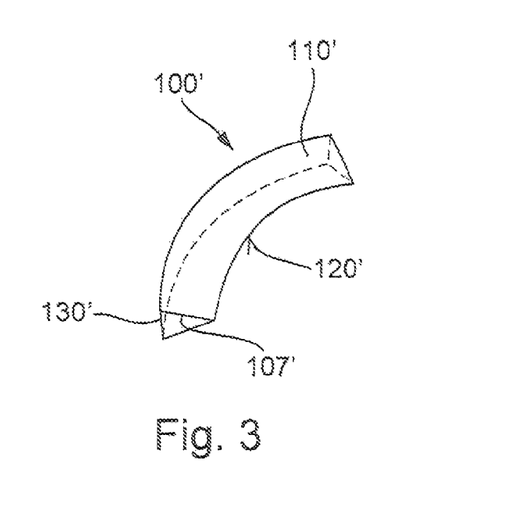
FIG. 3 shows a sectional angled view of artificial meniscus known from the prior art.

FIG. 3 schematically shows a sectional angled view of the artificial meniscus 100' represented in FIG. 2. It is clear from FIG. 3 that the artificial meniscus 100' is itself already elevated or has an elevation 107'.

Figure 4:
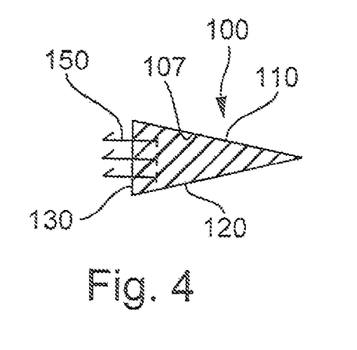
FIG. 4 shows a cross-sectional view of an implant with anchorage elements.

FIG. 4 shows the cross-sectional surface area of an implant 100. The implant 100 is based on an elevated molding 105 formed as an artificial meniscus or artificial partial meniscus (molding 105 itself has an elevation 107). The elevated molding 105 has a femoral condylar contact area 110, a tibial condylar contact area 120 and an articular capsule contact area 130 (base). The elevated molding 105 additionally has anchorage elements 150. As represented by way of example in FIG. 4, the anchorage elements 150 may take the form of flukes. The anchorage elements 150 are integrally connected to the elevated molding 105 and protruded from the articular capsule contact area 130 thereof. By means of the anchorage elements 150, the implant 100 can be fixed to the articular capsule or cartilage rim of a human or animal knee joint. In this case, during the anchoring in the articular capsule, the anchorage elements 150 provide with particular advantage targeted, controllable inflammation stimuli, which can speed up the anchorage of the implant 100, in particular the growing of body cells into the implant 100 and possibly the building-up of connective and/or supportive tissue, in particular cartilage tissue.

Figure 5:
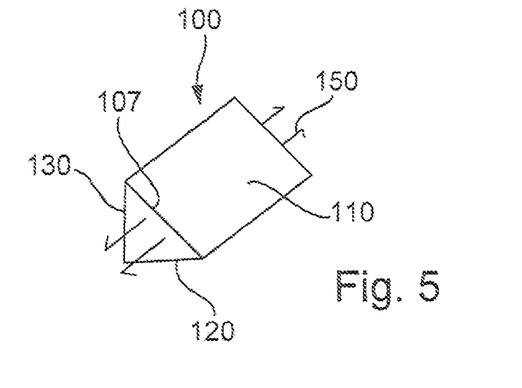
FIG. 5 shows a sectional angled view of an implant with anchorage elements.

FIG. 5 schematically shows a further implant 100. The implant 100 comprises an elevated molding 105, formed as an artificial partial meniscus (molding 105 itself has an elevation 107). The elevated molding 105 likewise has a femoral condylar contact area 110, a tibial condylar contact area 120 and an articular capsule contact area 130 (base). The elevated molding 105 is of a substantially wedge-shaped form and has anchorage elements 150 at the ends of the wedge that are respectively intended to be adjacent the natural residual meniscus. With respect to further features and advantages of the anchorage elements 150, reference is made to the description relating to FIG. 5.

Figure 6:
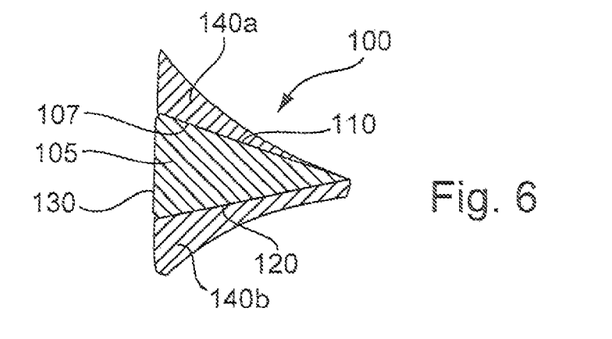
FIG. 6 shows a cross-sectional view of an implant with two additional elevations.

FIG. 6 shows the cross-sectional surface area of a preferred implant 100. The implant is based on an elevated molding 105 (molding 105 itself has an elevation 107). The elevated molding 105 has a femoral condylar contact area 110, a tibial condylar contact area 120 and an articular capsule contact area 130 (base). The elevated molding 105 may in this case be formed in particular as an artificial meniscus or artificial partial meniscus, as represented for example in FIG. 2. The implant 100 has two additional elevations 140a; b. These are formed as additional elevations on the molding that is itself already elevated, to be precise on the femoral condylar contact area 110 and tibial condylar contact area 120 of the elevated molding 105. The additional elevation 140a is concavely formed on its side facing the articular surface, in order that it can cooperate with a femoral condyle. The additional elevation 140b, on the other hand, is (slightly) convexly formed on its side facing the articular surface, in order that it can cooperate with a tibial condyle.

Figure 7:
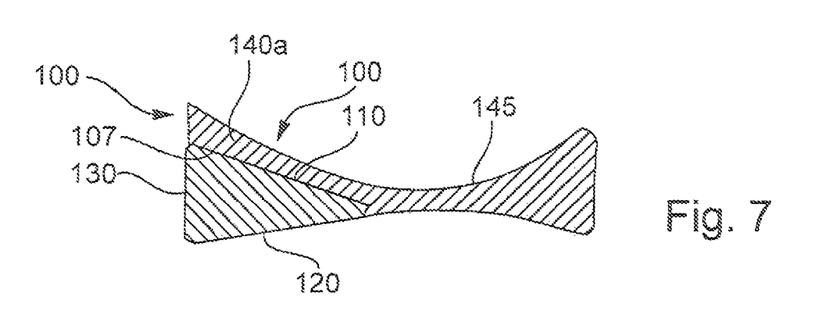
FIG. 7 shows a cross-sectional view of an implant with an additional elevation facing the femoral articular surface.

FIG. 7 shows a further preferred implant 100. Like the implant represented in FIG. 6, the implant 100 is based on an elevated molding 105, which may be formed in the manner of an artificial meniscus or artificial partial meniscus. The elevated molding 105 also has furthermore a femoral condylar contact area 110, a tibial condylar contact area 120 and an articular capsule contact area 130 (base). On the outer area of the elevated molding 105, an elevation 140*a* is additionally formed on the femoral condylar contact area. The additional elevation 140*a* has at the same time a spacer region 145, which protrudes between the femoral and tibial articular surfaces and may extend as far as the notch region of a knee joint. The additional elevation 140*a* is (slightly) concavely formed on its side facing the femoral articular surface, to be able to cooperate with a femoral condyle.

Figure 8:
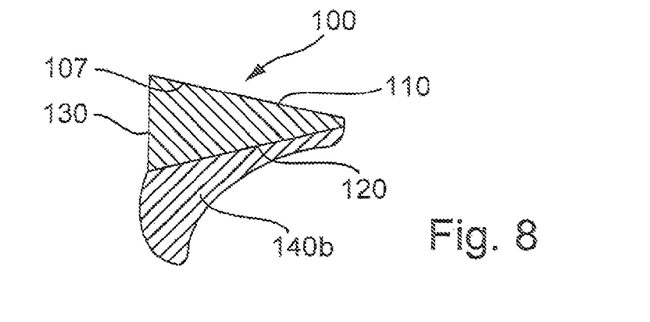
FIG. 8 shows a cross-sectional view of an implant with an additional elevation facing the tibial articular surface.
Figure 9:
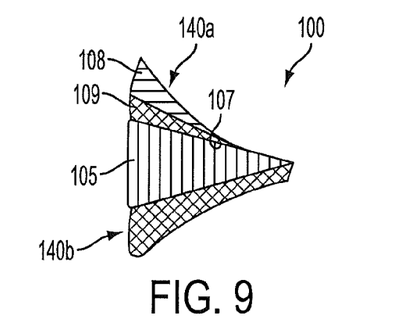
FIG. 9 shows a cross-sectional view of a implant with an additional elevation having a layered structure.
Figure 10:
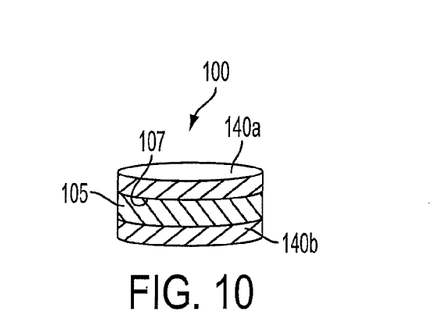
FIG. 10 shows an implant with a disk-shaped form.
Figure 11:
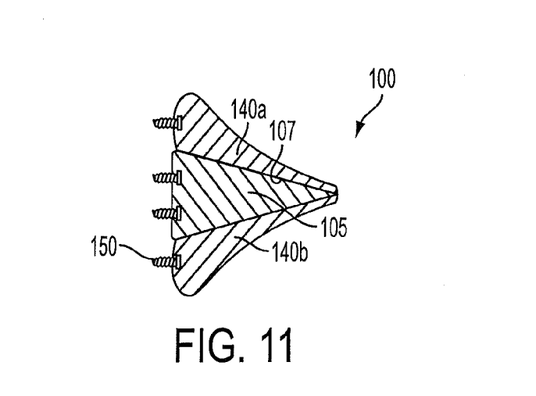
FIG. 11 shows an implant with anchor screws.

FIG. 8 schematically shows a further preferred implant 100. Like the implant represented in FIG. 7, the implant 100 is based on an elevated molding 105, which may be formed in the manner of an artificial meniscus or artificial partial meniscus. The elevated molding 105 likewise has a femoral condylar contact area 110, a tibial condylar contact area 120 and an articular capsule contact area 130 (base). On the outer area of the elevated molding 105, an elevation 140*b* is additionally formed on the tibial condylar contact area. The elevation 140*b* is (slightly) convexly formed on the side facing the tibial condylar contact area, to allow cooperation with a tibial conydyle. With respect to further features and details, reference is made to the description relating to FIG. 7. FIG. 9 shows an example of an implant 100 with at least an additional elevation 140*a* having a layered structure, as indicated by layers 108 and 109. FIG. 10 shows an example of an implant 100 with a disk-shaped form, in particular in the form of a cylindrical disk. FIG. 11 shows an example of an implant wherein the elevated molding and/or at least one additional elevation have anchor screws.

Although the apparatus has been described in connection with specific forms thereof, it will be appreciated that a wide variety of equivalents may be substituted for the specified elements described herein without departing from the spirit and scope of this disclosure as described in the appended claims.

The invention claimed is:

1. An implant for reconstructing meniscus defects or partial meniscus defects comprising an elevated molding with a femoral condylar contact area, a tibial condylar contact area and an articular capsule contact area, wherein the elevated molding extends in a transverse slope and at least one additional elevation is formed on an outer area of the elevated molding and wherein the elevated molding and the at least one additional elevation are formed in one piece, and wherein the elevated molding is of an open-pore form only in a region of its articular capsule contact area, wherein the elevated molding has a closed pore form in the femoral condylar contact area and/or tibial condylar contact area.

2. The implant as claimed in claim 1, having a compound structure comprising the elevated molding and the at least one additional elevation as a composite.

3. The implant as claimed in claim 1, wherein the elevated molding and the at least one additional elevation are connected to each other along a common boundary surface.

4. The implant as claimed in claim 1, wherein the at least one additional elevation is formed on the femoral condylar contact area, tibial condylar contact area and/or articular capsule contact area of the elevated molding.

5. The implant as claimed in claim 1, which is completely resorbable.

6. The implant as claimed in claim 1, wherein the at least one additional elevation is formed from a different material than the elevated molding.

7. The implant as claimed in claim 1, wherein the at least one additional elevation is formed from a more quickly resorbable material than the elevated molding.

8. The implant as claimed in claim 1, wherein the at least one additional elevation has a layered structure formed from materials with different resorption rates.

9. The implant as claimed in claim 8, wherein layers of the at least one additional elevation form a resorption gradient, the resorption rate of the layers increasing substantially continuously from a side of the at least one additional elevation that is facing elevated molding to an opposite side of the at least one additional elevation.

10. The implant as claimed in claim 1, wherein the at least one additional elevation is formed from a softer, more elastic material than the elevated molding.

11. The implant as claimed in claim 1, wherein the at least one additional elevation is an open-pore form.

12. The implant as claimed in claim 1, wherein the at least one additional elevation contains closed pores.

13. The implant as claimed in claim 1, wherein the elevated molding and/or the at least one additional elevation have open pores that are at least partially filled with a resorbable and/or viscous material.

14. The implant as claimed in claim 1, wherein elevated molding and/or the at least one additional elevation is of a disk-shaped, semicircular, sickle-shaped or crescent-shaped form.

15. The implant according to claim 1, wherein the elevated molding and/or the at least one additional elevation has anchorage elements selected from the group consisting of anchor hooks, anchor flukes, anchor pins, anchor screws, filamentary structures and combinations thereof.

16. The implant as claimed in claim 1, wherein the elevated molding and/or the at least one additional elevation is formed from a natural polymer or biopolymer and/or synthetic polymer selected from the group comprising proteins, polysaccharides, polyhydroxyalkanoates, polyvinyl alcohol, polyurethanes and combinations thereof.

17. The implant as claimed in claim 1, wherein the elevated molding and/or the at least one additional elevation is inoculated with autologous body cells, selected from the group consisting of chondrocytes, chondroblasts, synovial cells, fibroblasts, precursor cells thereof, stem cells thereof and combinations thereof.

18. The implant as claimed in claim 1, wherein the elevated molding and/or the at least one additional elevation has a proportion of a fibrous material.

19. The implant as claimed in claim, having a proportion of the fibrous material of between 2 and 80% by weight based on the overall weight of the implant.

20. A surgical set for reconstructing meniscus defects or partial meniscus defects, comprising at least one implant as claimed in claim 1.

21. An implant for reconstructing meniscus defects or partial meniscus defects comprising an elevated molding with a femoral condylar contact area, a tibial condylar contact area and an articular capsule contact area, wherein the elevated molding has a wedge-shaped form and at least one additional elevation is formed on an outer area of the elevated molding and wherein the elevated molding and the at least one additional elevation are formed in one piece, and wherein the elevated molding is of an open-pore form only in a region of its articular capsule contact area, wherein the elevated molding has a closed pore form in the femoral condylar contact area and/or tibial condylar contact area.

* * * * *